United States Patent
Keall et al.

(10) Patent No.: US 8,849,373 B2
(45) Date of Patent: Sep. 30, 2014

(54) METHOD AND APPARATUS FOR REAL-TIME 3D TARGET POSITION ESTIMATION BY COMBINING SINGLE X-RAY IMAGING AND EXTERNAL RESPIRATORY SIGNALS

(75) Inventors: Paul J. Keall, Stanford, CA (US); Amit Sawant, Los Altos, CA (US); Peter Maxim, Palo Alto, CA (US); Yelin Suh, Palo Alto, CA (US); Lei Xing, Palo Alto, CA (US); Billy W. Loo, Jr., Foster City, CA (US); Byung Chul Cho, Palo Alto, CA (US)

(73) Assignee: Stanford University, Palo Alto, CA (US)

( * ) Notice: Subject to any disclaimer, the term of this patent is extended or adjusted under 35 U.S.C. 154(b) by 827 days.

(21) Appl. No.: 12/119,464

(22) Filed: May 12, 2008

(65) Prior Publication Data
US 2008/0281192 A1 Nov. 13, 2008

Related U.S. Application Data

(60) Provisional application No. 60/917,637, filed on May 11, 2007.

(51) Int. Cl.
| | |
|---|---|
| *A61B 5/00* | (2006.01) |
| *A61B 6/03* | (2006.01) |
| *A61B 6/12* | (2006.01) |
| *A61B 6/06* | (2006.01) |
| *A61B 5/08* | (2006.01) |
| *A61B 6/00* | (2006.01) |

(52) U.S. Cl.
CPC ............... *A61B 6/032* (2013.01); *A61B 6/541* (2013.01); *A61B 6/12* (2013.01); *A61B 6/06* (2013.01); *A61B 5/08* (2013.01)
USPC ........... 600/424; 600/425; 600/426; 600/427; 600/428

(58) Field of Classification Search
USPC .......................... 600/424–428; 382/128, 131
See application file for complete search history.

(56) References Cited

U.S. PATENT DOCUMENTS

| 6,144,875 A * | 11/2000 | Schweikard et al. ......... 600/427 |
| 6,501,981 B1 * | 12/2002 | Schweikard et al. ......... 600/427 |
| 7,260,426 B2 * | 8/2007 | Schweikard et al. ......... 600/407 |
| 7,570,738 B2 * | 8/2009 | Khamene et al. ............... 378/65 |
| 7,620,444 B2 * | 11/2009 | Le et al. ........................ 600/428 |
| 2008/0021300 A1 * | 1/2008 | Allison ......................... 600/407 |
| 2008/0081991 A1 * | 4/2008 | West et al. .................... 600/425 |

\* cited by examiner

*Primary Examiner* — Peter Luong
(74) *Attorney, Agent, or Firm* — Whitham, Curtis, Christofferson & Cook, P.C.

(57) ABSTRACT

A method and system are disclosed for estimating internal position information of a target in real-time based on a single gantry-mounted x-ray imager and a respiratory signal. The x-ray imaging is done periodically to limit radiation dosage. Initial parameters for the estimation model are determined in a pre-treatment session using four dimensional computed tomography (4D CT) in combination with a respiratory signal acquired from the patient. The model parameters are updated during treatment based on the periodic x-ray image data and the respiratory signal.

20 Claims, 2 Drawing Sheets

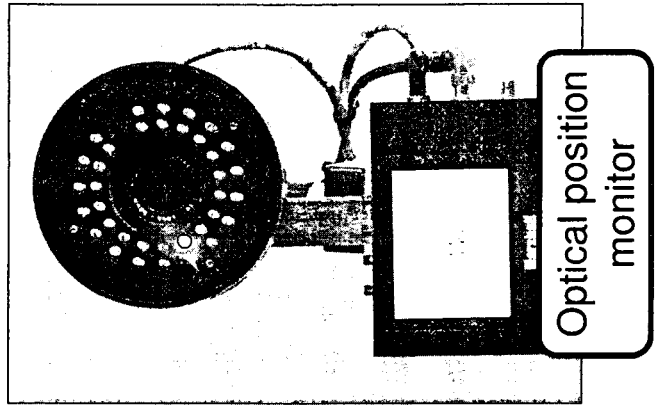
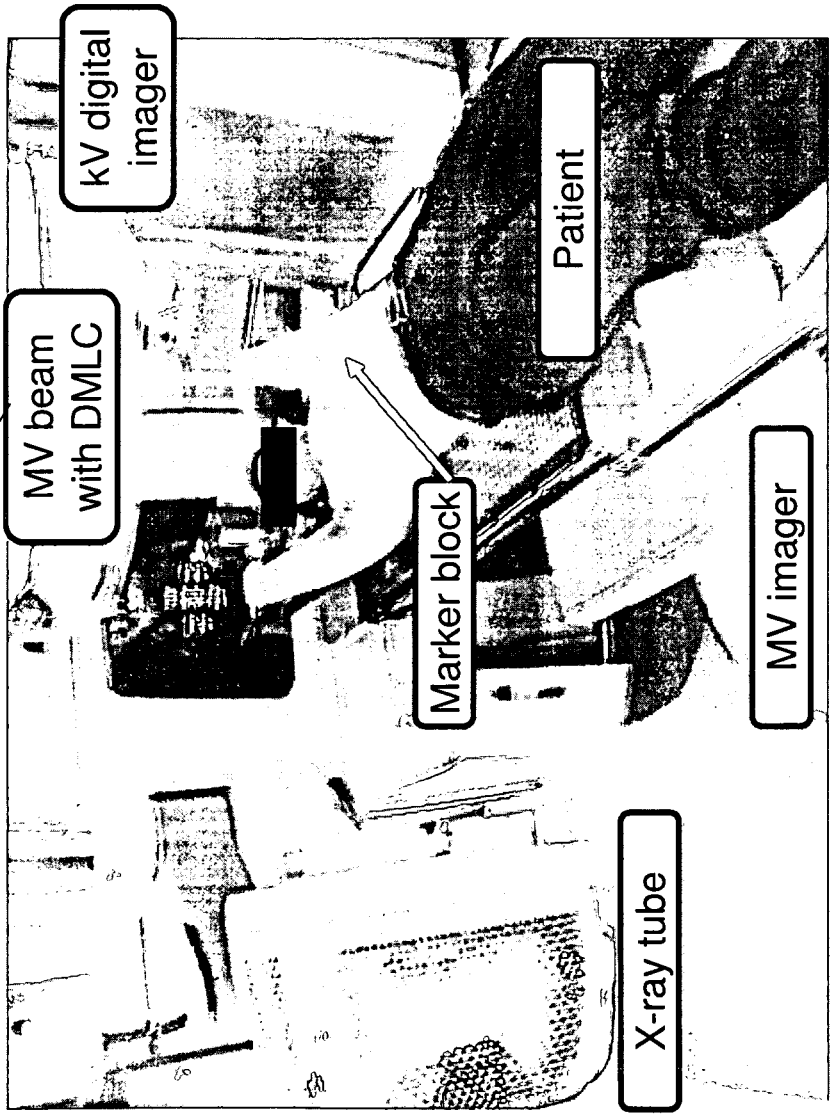
Figure 2B
Figure 2A

METHOD AND APPARATUS FOR REAL-TIME 3D TARGET POSITION ESTIMATION BY COMBINING SINGLE X-RAY IMAGING AND EXTERNAL RESPIRATORY SIGNALS

This application claims the benefit of U.S. Provisional Application No. 60/917,637 of the same title filed on May 11, 2007.

FEDERALLY-SPONSORED RESEARCH OR DEVELOPMENT

This invention was made with Government support under contract CA093626 awarded by the National Institutes of Health. The Government has certain rights in this invention.

BACKGROUND OF THE INVENTION

1. Field of the Invention

The present invention generally relates to radiotherapy, and in particular to methods for estimating internal target position for use by systems able to continuously align a radiation beam with the target.

2. Background Description

Real-time internal target position estimation is of high interest in radiotherapy, particularly with the recent development of robotic, linear accelerator, DMLC and couch-based systems which can continuously align the radiation beam with the target. It would make an important contribution to effective use of these systems to develop an algorithm to combine x-ray and external respiratory monitoring sources for estimating real-time target position. Currently, there is no system in radiotherapy to estimate internal position from a single x-ray imager and an optical system. What is needed is a methodology for combining x-ray and external respiratory sources for estimating real-time target position.

SUMMARY OF THE INVENTION

It is therefore an object of the invention to provide a methodology for combining x-ray and external respiratory sources for estimating target position in real-time.

An aspect of the invention is a method for real-time position estimation of an oncology target in a patient, the method comprising continuous monitoring of a respiratory signal of the patient; imaging of the target using a single imaging device, the imaging being done periodically to limit radiation dosage administered by the single imaging device; applying a model to estimate a centroid position of the target from a combination of the respiratory signal and target position data from the imaging; determining and updating parameters of the model by using position displacement data from the imaging; and using the updated model in real-time to apply a treatment program.

A further aspect of the invention is the optional implanting of a marker in the patient and then using the location information of the marker obtained in the periodic imaging to improve accuracy of the target position data. It is also an aspect of the invention to adjust the periodicity of imaging to implement a tradeoff between position estimation accuracy and said radiation dosage limitation.

Yet another aspect of the invention is to make an initial determination of the model parameters in a pre-treatment session by using four dimensional computed tomography (4D CT) or four dimensional cone beam computed tomography (4D CBCT). In a preferred embodiment the imaging device is an X-ray machine, and more particularly a linear accelerator.

BRIEF DESCRIPTION OF THE DRAWINGS

The foregoing and other objects, aspects and advantages will be better understood from the following detailed description of a preferred embodiment of the invention with reference to the drawings, in which:

Table 1 is a list of linear accelerator vendors, their configurations and comments on the applicability of using a single x-ray imager and respiratory monitoring system to determine target position.

Figure 1:
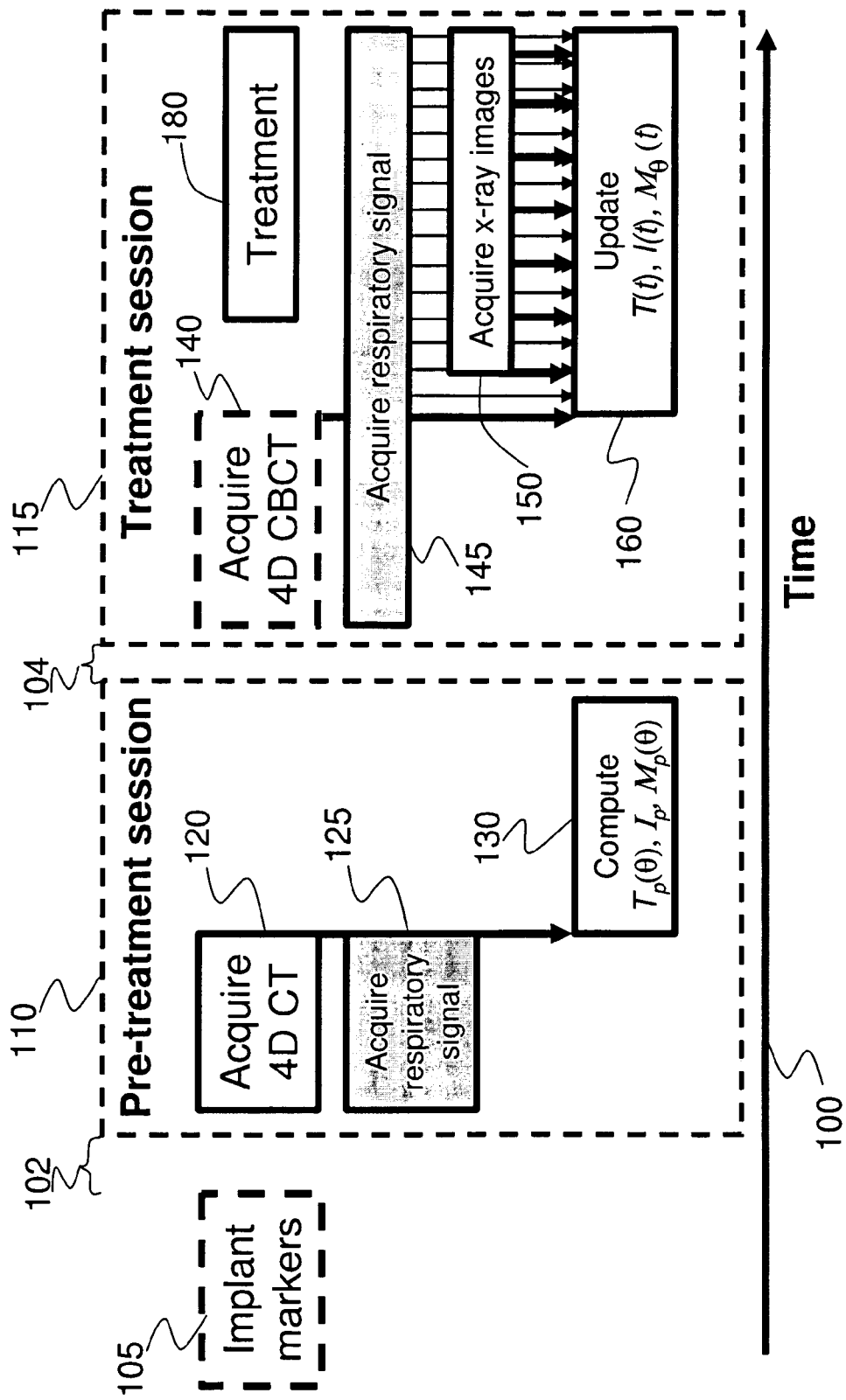

Table 2 is a list of terms with their symbols and descriptions.

FIG. 1 is a schematic of the estimation process.

FIG. 2A is a schematic of the components of the planned experimental system to test the target position estimation algorithm; FIG. 2B shows the optical position monitor component.

DETAILED DESCRIPTION OF A PREFERRED EMBODIMENT OF THE INVENTION

Real-time internal target position estimation is of high interest in radiotherapy, particularly with the recent development of robotic, linear accelerator, DMLC (Dynamic Multi-Leaf Collimation) and couch-based systems which can continuously align the radiation beam with the target. To estimate the internal target position, one interesting approach is to combine x-ray images with respiratory monitoring. X-ray images give internal anatomic information, particularly if radio-opaque objects such as implanted markers are used. However, this procedure also gives additional radiation dose to the patient.

Respiratory monitoring gives a motion signal without additional ionizing radiation but does not yield target position information. The current invention focuses on the use of a single x-ray imager with 4D CT or 4D CBCT prior information. Note that a methodology for this approach with orthogonal simultaneous x-ray imagers and without 4D CT information has been developed and is commercially available. Simultaneous imaging from multiple directions can be considered an extension of the current algorithm where the time difference between acquired images at different angles is small or zero.

The reason for choosing a single imager and respiratory signal configuration is its high accuracy (an overall accuracy from the 160 3D tumor motion data in seen to be within an average rms error of 1 mm for the entire data set and 1.5 mm for datasets in which the average tumor motion is over 5 mm per respiratory cycle), compromise between radiation dose and position monitoring accuracy and widespread applicability to commercially available linear accelerator (and potentially proton accelerator) designs, as explained in Table 1. Also, there are many commercially available sources of respiratory signal, including optical monitoring, strain gauge, pressure sensor, nasal thermometer and spirometer.

This invention describes an algorithm to combine x-ray and external respiratory monitoring sources for estimating real-time target position.

In the scenario contemplated by the invention, there is a quasi-continuous external position measurement, and occasional internal position measurements. This approach can be generalized to cover multiple sources of the internal position. The objective is accurate and precise estimates of internal position quasi-continuously.

It is assumed that internal and external motion have the same basis function, F, but differences in position, motion ratio and time lag/lead (phase differences) have been observed. The form of F will be different for different patients, and we do not wish to characterize this as a given function, e.g. sinusoidal. However, the form of F will be characterized by a period (which can change), because this is necessary for estimates as described below.

Thus we can formulate:

$$I(t) = x_I + a_I F(t + \Delta t)$$

$$E(t) = x_E + a_E F(t)$$

Using the discrete measurements of $\tilde{I}$ and $\tilde{E}$ at n discrete time points, $i \in \{1:n\}$ spanning an integral number of respiratory cycles (e.g. 4D CT or fluoroscopy data), we wish to build a model for $\hat{I}(t)$ based on E(t).

Thus $$\hat{I}(t) = x_I - x_E + \frac{a_I}{a_E} E(t - \Delta t).$$

$x_I$ and $x_E$ can be found from the mean of $\tilde{I}$ and $\tilde{E}$ respectively.

$$\frac{a_I}{a_E}$$

can be estimated from the dispersion of $\tilde{I}/\tilde{E}$. $\Delta t$ is estimated by maximizing the correlation between $\hat{I}(t)$ and $\tilde{I}$ over the same sampling period which also gives an estimate of the lower bound of the uncertainty.

Generalizing to different directions with different $\Delta t$ values will result in hysteresis.

The present invention describes an algorithm to combine x-ray and external respiratory monitoring sources for estimating real-time target position. The target position with respect to the linac isocenter, $\hat{T}(t)$, can be calculated using the general equation $\hat{T}(t) = \hat{I}(t) + \hat{M}_\theta(t) R(t)$, where $\hat{I}(t)$ is the estimate of the internal/external displacement at time t, $\hat{M}_\theta(t)$ is the estimated motion relationship between internal motion and external motion as a function of phase at time t and R(t) is the external respiratory signal. The coefficients of $\hat{I}(t)$ and $\hat{M}_\theta(t)$ are updated periodically using the 2D target position from the x-ray projection, $\hat{T}(t)_{2D}^{g,c}$. The initial coefficient values are given from 4D CT (Four Dimensional Computed Tomography) or 4D CBCT (Cone Beam Computed Tomography). An estimate of the optimal operating characteristics of the invention may be made using a cost-benefit analysis of the trade-off of accuracy versus imaging dose.

Method Description

For clarity a definition of terms is given in Table 2. A schematic of the estimation process is given in FIG. 1, with an example application to a treatment shown in FIGS. 2A and 2B. FIG. 1 shows a timeline 100, with procedures for a pre-treatment session 110 and a treatment session 115. In the pre-treatment session 110, a 4D CT analysis is acquired 120, along with respiratory signal 125, and from these inputs computations 130 are made for $T_p(\theta)$, $I_p$ and $M_p(\theta)$ After 104 the pre-treatment session 110, the treatment session begins with acquisition of the respiratory signal 145, periodic acquisition of X-ray images 150, which are used to update 160 parameters for the model terms T(t), I(t) and $M_\theta(t)$. Treatment 180 then proceeds, with real-time updating of the model terms using the acquired respiratory signal 145 and the periodically acquired X-ray images 150. The acquisition of 4D CBCT data 140 during the treatment session 115 is optional (as indicated by the dashed line), but if acquired will give additional information useful to assist in predicting the internal position. Implanting radio-opaque markers 105 prior 102 to the pre-treatment session 110 is also optional, as an alternative to techniques to more robustly segment internal anatomy without implanted markers.

The aim of position monitoring is to estimate the target centroid position with respect to the linac (linear accelerator) isocenter, $\hat{T}(x,y,z,t) \equiv \hat{T}(t)$, throughout a course of therapy. In principle, position monitoring can be used to generate higher dimensionality information rather than just an estimated target position. However such monitoring will be the subject of future research.

General Formalism

In order to reduce dose the x-ray imager is triggered periodically (rather than continuously) to determine and update the model parameters used to estimate $\hat{T}(t)$ based on the measured respiratory signal, $\hat{R}(t)$ The target position with respect to the linac isocenter, $\hat{T}(t)$, is calculated using the general equation:

$$\hat{T}(t) = \hat{I}(t) + \hat{M}_\theta(t) R(t) \tag{1}$$

Note that $\hat{I}(t)$ could be incorporated directly into $\hat{M}_\theta(t)$, however given the potentially large variation between $\tilde{I}_p$ and $\hat{I}(t)$ (e.g. due to a change in the day to day position of the respiratory monitor) this displacement was included separately.

Initial Estimates

The initial estimates of the parameters for equation (1) are acquired from the 4D CT (or 4D CBCT) scan. For each phase of the 4D CT scan the external signal position and internal position are computed. Thus $\tilde{I}_p$, $\tilde{M}_p(\theta)$ and $\tilde{T}_p(\theta)$ are determined, and an initial discretized form of $\tilde{M}_p(\theta)$ is obtained. However, as the phase is continually changing with time, an appropriate curvilinear relationship is obtained to ensure $M_p(\theta)$ is continuous over $[0,2\pi)$.

Periodic Updating

It is assumed that the internal/external relationship changes with time (otherwise the initial information obtained from the 4D CT scan would be sufficient and no further imaging would be necessary). In general, a single planar x-ray image will not be able to resolve the marker positions along the beam axis, so there will be some residual uncertainty in the estimation of the marker position.

The coefficients of $\hat{I}(t)$ and $\hat{M}_\theta(t)$ are updated with information from the projection images, through $\hat{T}(t)_{2D}^{g,c}$ where the update of the coefficients are weighted by the resolving power, i.e. for an anterior-posterior (AP) aligned imager the superior-inferior coefficients can be updated however the AP coefficients remain the same. As the gantry rotates, all of the coefficients will be updated. Differences between the estimated position $\hat{T}(t)$, projected along the same gantry angle as the imager and couch angle as the patient, and $\hat{T}(t)_{2D}^{g,c}$, are used to update the correlation model.

Any feedback system has a finite response time. The foregoing system and method can be implemented with motion prediction to account for this response time, depending on the time for computation and response device used for these calculations.

While the invention has been described in terms of preferred embodiments, those skilled in the art will recognize that the invention can be practiced with modification within the spirit and scope of the appended claims.

TABLE 1

| Vendor/Linac | Configuration | Comments |
| --- | --- | --- |
| Accuray/Cyberknife | Dual room-mounted x-ray imagers | Proposed monitoring system can be used to: Allow additional anterior and posterior beam arrangements, currently prohibited as robot can obscure a single imager for some beam positions. Reduce imaging dose in certain situations by using only single imaging mode rather than dual mode |
| BrainLab/Novalis | Dual room-mounted x-ray imagers | X-ray imagers cannot be used simultaneously due to a single generator, hence proposed position monitoring applicable to be run in parallel |
| Elekta/Synergy | Single gantry-mounted x-ray imager | Imager orthogonal to MV treatment beam |
| Siemens/Artiste | Single gantry-mounted x-ray imager | Imager inline with MV treatment beam |
| Tomotherapy/HiArt | Single gantry-mounted x-ray imager | Original design though not in current commercial implementation |
| Varian/Trilogy | Single gantry-mounted x-ray imager | Imager orthogonal to MV treatment beam |

TABLE 2

| Name | Symbol | Description |
| --- | --- | --- |
| Internal-external displacement from planning | $\tilde{I}_p$ | A vector relating (e.g. the mean) the displacement between internal target position with the external respiratory signal from the 4D CT (or 4D CBCT) scan. |
| Internal-external displacement | $\hat{I}(t)$ | Estimate (e.g. the mean) of the internal/external displacement at time t. |
| Internal external motion relationship from planning | $\tilde{M}_p(\theta)$ | Motion relationship between internal motion and external motion as a function of phase from the 4D CT. |
| Internal external motion relationship | $\hat{M}_\theta(t)$ | Estimated motion relationship between internal motion and external motion as a function of phase at time t. |
| External respiratory signal | $R(t)$ | External respiratory signal at time t. Note that R can have 1-3 dimensions and can contain both phase, position and rotation information. Only position and phase information is used here. Position is measured, and phase is estimated from the measurements in real-time. |
| Target position as a function of phase calculated from 4D CT | $\tilde{T}_p(\theta)$ | Target position as a function of phase measured from 4D CT. The internal position will be spatially related to a landmark visible with a single planar imager, such as one or more implanted markers. |
| Estimated target position | $\hat{T}(t)$ | Internal respiratory position as estimated. |
| 2D target projection | $\tilde{T}(t)_{2D}{}^{g,c}$ | Internal respiratory position as measured by a planar imager at time t with the imager at gantry angle g and patient at couch angle c. |

Having thus described our invention, what we claim as new and desire to secure by Letters Patent is as follows:

1. A method for real-time position estimation of an oncology target in a patient, comprising:
continuous monitoring of a respiratory signal of the patient;
imaging of the target using an imaging device having a single source, the imaging being done periodically to limit radiation dosage administered by the single imaging device, each periodic image of the target being taken at a articular time from a corresponding particular direction with respect to the target;
applying a model to estimate at the particular time for each said corresponding periodic image a centroid position of the target from a combination of said respiratory signal and target position data from said imaging;
determining parameters of said model by using position displacement data from said imaging; and
applying said model in real-time to a treatment program.

2. A method as in claim 1, further comprising:
implanting a marker in the patient;
using location information of the marker obtained in said periodic imaging to improve accuracy of said target position data; and
updating said model parameters using position displacement data from said imaging and adjusting a periodicity of said imaging to implement a tradeoff between position estimation accuracy and said radiation dosage limitation.

3. A method as in claim 1, further comprising using one of the group four dimensional computed tomography (4D CT) and four dimensional cone beam computed tomography (4D CBCT) as the single imaging device a) in a pre-treatment session to initially determine said model parameters and b) during the treatment program to update said model parameters.

4. A method as in claim 1, wherein the imaging device is an X-ray machine.

5. A method as in claim 4, wherein the X-ray machine is a linear accelerator (linac).

6. A method as in claim 1, further comprising using at least one additional imaging device for acquiring an additional image simultaneously at a different angle.

7. A method as in claim 1, further comprising using one of the group four dimensional computed tomography (4D CT) and four dimensional cone beam computed tomography (4D CBCT) to provide additional information to improve said position estimation accuracy.

8. A method as in claim 1, wherein the model is $$\hat{T}(t)=\hat{I}(t)+\hat{M}_\theta R(t),$$

where the target centroid position is $\hat{T}(x, y, z, t)=\hat{T}(t)$,
$R(t)$ is the measured respiratory signal over time, $\hat{I}(t)$ is the estimated displacement over time between the internal target position and the external respiratory signal, and $\hat{M}_\theta(t)$ is the estimated motion relationship between internal motion and external motion as a function of phase over time, and
wherein the coefficients of $\hat{I}(t)$ and $\hat{M}_\theta(t)$ are updated using two dimensional position displacement data $\tilde{T}(t)_{2D}{}^{g,c}$ from said periodic imaging.

9. A method as in claim 8, wherein said update of the coefficients are weighted by a resolving power.

10. A method as in claim 1, wherein said model accounts for finite response time delays between said monitoring and said imaging and consequent application of said model updates to said treatment program.

11. A system for real-time position estimation of an oncology target in a patient, comprising:
a respiratory signal of the patient;
an imaging device having a single source for imaging the target, the imaging being done periodically to limit radiation dosage administered by the single source imaging device, each periodic image of the target being taken at a particular time from a corresponding particular direction with respect to the target;

a model for estimating at the particular time for each said corresponding periodic image a centroid position of the target from a combination of said respiratory signal and target position data from said imaging; and parameters of said model determined and updated by using position displacement data from said imaging;

wherein said model is applied in real-time to a treatment program.

12. A system as in claim 11, further comprising:
a marker implanted in the patient;
wherein location information of the marker obtained in said periodic imaging is used to improve accuracy of said target position data.

13. A system as in claim 11, further comprising one of the group four dimensional computed tomography (4D CT) and four dimensional cone beam computed tomography (4D CBCT) used as the single imaging device a) in a pre-treatment session to initially determine said model parameters and b) during the treatment program to update said model parameters.

14. A system as in claim 11, wherein the imaging device is an X-ray machine.

15. A system as in claim 14, wherein the X-ray machine is a linear accelerator (linac).

16. A system as in claim 11, further comprising at least one additional imaging device for acquiring an additional image simultaneously at a different angle.

17. A system as in claim 11, further comprising one of the group four dimensional computed tomography (4D CT) and four dimensional cone beam computed tomography (4D CBCT) for providing additional information to improve said position estimation accuracy.

18. A system as in claim 11, wherein the model is $$\hat{T}(t)=\hat{I}(t)+\hat{M}_\theta R(t),$$

where the target centroid position is $\hat{T}(x, y, z, t) \equiv \hat{T}(t)$,
$R(t)$ is the measured respiratory signal over time, $\hat{I}(t)$ is the estimated displacement over time between the internal target position and the external respiratory signal, and $\hat{M}_\theta(t)$ is the estimated motion relationship between internal motion and external motion as a function of phase over time, and wherein the coefficients of $\hat{I}(t)$ and $\hat{M}_\theta(t)$ are updated using two dimensional position displacement data $\hat{T}(t)_{2D}^{g,c}$ from said periodic imaging.

19. A system as in claim 18, wherein said update of the coefficients are weighted by a resolving power.

20. A system as in claim 11, wherein said model accounts for finite response time delays between said monitoring and said imaging and consequent application of said model updates to said treatment program.

* * * * *